United States Patent [19]

Woods

[11] 4,258,044
[45] Mar. 24, 1981

[54] FUNGICIDAL HALOALKYL POLYHALOQUINOXALINE SULFONATES

[75] Inventor: Thomas S. Woods, Wilmington, Del.

[73] Assignee: E. I. Du Pont de Nemours and Company, Wilmington, Del.

[21] Appl. No.: 42,554

[22] Filed: May 25, 1979

[51] Int. Cl.³ .................. C07D 241/44; A61K 31/495
[52] U.S. Cl. ..................................... 424/250; 544/356
[58] Field of Search ......................... 544/356; 424/250

[56] References Cited

U.S. PATENT DOCUMENTS

| | | | |
|---|---|---|---|
| 3,355,352 | 11/1967 | Hattori | 544/356 |
| 3,478,027 | 11/1969 | Paulus | 544/356 |

FOREIGN PATENT DOCUMENTS

| | | | |
|---|---|---|---|
| 1194631 | 6/1965 | Fed. Rep. of Germany | 544/356 |
| 39-27255 | 11/1964 | Japan | 544/356 |
| 40-12317 | 6/1965 | Japan | 544/356 |
| 40-23196 | 10/1965 | Japan | 544/356 |

*Primary Examiner*—Mark L. Berch

[57] ABSTRACT

Haloalkyl polyhaloquinoxaline sulfonate compounds of the formula

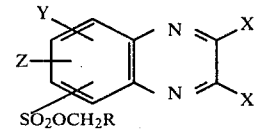

are useful as fungicides.

43 Claims, No Drawings

FUNGICIDAL HALOALKYL POLYHALOQUINOXALINE SULFONATES

BACKGROUND OF THE INVENTION

This invention relates to compounds having useful agricultural properties. In particular, this invention relates to polyhaloquinoxaline sulfonates having useful fungicidal properties.

Japanese Patent Application Publication No. 40-23196 issued on Oct. 13, 1965 discloses agricultural fungicides having as an effective component one or more of the compounds represented by the following general formula,

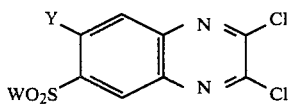

II where Y is H and W is SR with R representing a lower alkyl group. The disclosed compounds are stated to be particularly useful against certain rice crop diseases. Japanese Patent Application Publication No. 39-27255 issued on Nov. 28, 1964 discloses compounds of formula II wherein W is OR, with R representing a lower alkyl group, and Y is hydrogen, halogen, lower alkyl or lower alkoxy. The compounds are disclosed to be useful as agricultural chemicals, drugs, and the like, and as intermediates. Belgian Patent No. 635,579 issued on Nov. 14, 1963 discloses compounds of formula II wherein Y is hydrogen and W is a $NR_1R_2$ group with $R_1$ and $R_2$ being hydrogen, aryl, or cyclohexyl, or $NR_1R_2$ taken together are morpholino or piperidino. The compounds are disclosed to be useful as fungicides.

Canadian Patent No. 13,562 discloses compounds of general formula III wherein X is Cl or Br; W is SCX'Y'R' with X' and Y' being oxygen or sulfur and R' being substituted alkyl, aralkyl, cycloalkyl, or aryl; Y is a group inert to acid halides; and n is 0–4. Acaricidal and fungicidal utility is disclosed for the compounds.

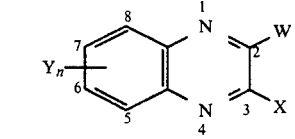

III

Japanese Patent Application Publication Number 12317/65 discloses compounds of formula III wherein W is AB with A being oxygen or sulfur and B being lower alkyl, alkenyl, hydroxyalkyl, or optionally substituted phenyl or benzyl; X is the same as W or is Cl; n is 1; and Y is 6-$NO_2$. The compounds are disclosed as having useful fungicidal activity. Germany Patent No. 1,194,631 discloses compounds of formula III wherein X, Y and W are Cl and n is 0–4; said compounds being useful as fungicides.

There is a constant need in the art for new fungicides, particularly those having improved or increased activity. Fungicidal compounds which provide increased activity but yet impart little or no injury to the host plants are even more desirable.

SUMMARY OF THE INVENTION

There are disclosed compounds of the formula

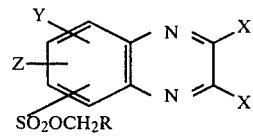

I wherein
X is F, Cl, or Br;
R is fluoroalkyl of 1–4 carbon atoms and 1–9 fluorine atoms or —$CCl_3$;
Y is H, F, Cl, Br, $CH_3$, $CF_3$, $CCl_3$, or $NO_2$; and
Z is H, F, Cl, Br, $CH_3$, $CF_3$, or $CCl_3$; with the proviso that when R is —$CCl_3$, Y is H, F, Cl or Br and Z is H. There are also disclosed agricultural compositions containing a compound of formula I and methods of using these compounds as fungicides.

DETAILED DESCRIPTION OF THE INVENTION

The compounds of the invention are haloalkyl-polyhaloquinoxaline sulfonate compounds of general formula I.

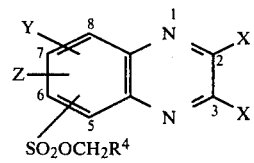

wherein
X is F, Cl, or Br;
R is fluoroalkyl of 1–4 carbon atoms and 1–9 fluorine atoms or —$CCl_3$;
Y is H, F, Cl, Br, $CH_3$, $CF_3$, $CCl_3$ or $NO_2$; and
Z is H, F, Cl, Br, $CH_3$, $CF_3$ or $CCl_3$; with the proviso that when R is —$CCl_3$, Y is H, F, Cl or Br and Z is H.

Compounds of the invention which are preferred because of their activity are those wherein X is Cl. Also preferred are compounds where Z is H and compounds having —$RCH_2OSO_2$— in the 6-position, i.e., $RCH_2OSO_2$— is a 6-substituent. More preferred compounds include those where X is Cl and $RCH_2OSO_2$— is in the 6-position and compounds which in addition have Z equal to H. Most preferred compounds of the invention included those where (a) X is Cl and $RCH_2OSO_2$— is a 6-substituent with R being perfluoroalkyl of 1–4 carbon atoms or —$(CF_2)_3CHF_2$; and (b) compounds which in addition have Z equal to H. Also, included among the most preferred compounds are compounds of group (a) and (b) wherein Y is H, F, Cl, or $CH_3$ and wherein additionally Y is in the 7-position, i.e., Y is a 7-substituent, and R is —$CF_3$.

Specifically preferred compounds are
2,3,7-trichloro-6-quinoxalinesulfonic acid, 2,2,2-trifluoroethyl ester;
2,3-dichloro-7-fluoro-6-quinoxalinesulfonic acid, 2,2,2-trifluoroethyl ester;
2,3-dichloro-7-fluoro-6-quinoxalinesulfonic acid, 2,2,3,3,3-pentafluoropropyl ester;
2,3,7-trichloro-6-quinoxalinesulfonic acid, 2,2,3,3,3-pentafluoropropyl ester;
2,3-dichloro-6-quinoxalinesulfonic acid, 2,2,3,3,3-pentafluoropropyl ester;

2,3-dichloro-7-fluoro-6-quinoxalinesulfonic acid, 2,2,3,3,4,4,4-heptafluorobutyl ester;
2,3-dichloro-7-fluoro-6-quinoxalinesulfonic acid, 2,2,3,3,4,4,5,5-octafluoropentyl ester;
2,3-dichloro-7-methyl-6-quinoxalinesulfonic acid, 2,2,2-trifluoroethyl ester;
2,3-dichloro-7-methyl-6-quinoxalinesulfonic acid, 2,2,3,3,3-pentafluoropropyl ester;
2,3-dichloro-6-quinoxalinesulfonic acid, 2,2,2-trifluoroethyl ester.

The compounds of the invention provide excellent disease control of several economically significant cropinfesting pathogens, especially apple scab and Grape Downy mildew, at low application rates with little or no injury to the host plants.

SYNTHESIS

Compounds of the invention wherein X is Cl or Br can be made by the process represented by the equation below.

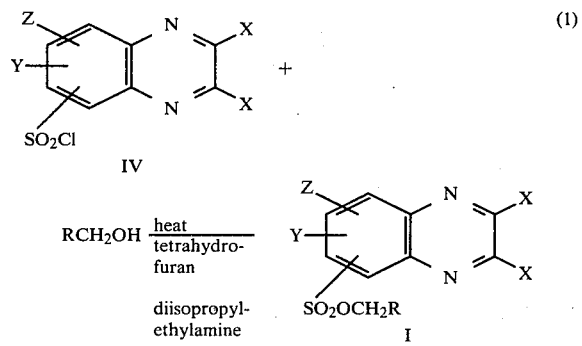

A sulfonyl chloride of formula IV is mixed with a haloalcohol in a suitable solvent, such as tetrahydrofuran, dioxane, or chloroform, and a suitable organic base, such as diisopropylethylamine or triethylamine, is added. The resulting reaction mixture is heated to a temperature of from about 50°–100° C. until the reaction is complete.

Starting material of formula IV wherein X is chlorine is prepared by suitable modification of the method disclosed in Japanese Patent Application Publication Number 40-27,257 (see Chem. Abstr. 63, 7019h (1965)). Thus, the desired 2,3-dichloroquinoxalinesulfonyl chloride is made by chlorination of the corresponding 1,2,3,4-tetrahydro-2,3 dioxoquinoxalinesulfonyl chloride in the presence of a phosphorus oxychloride and phosphorus pentachloride mixture as a promoter. The 1,2,3,4-tetrahydro-2,3-dioxoquinoxalinesulfonyl chloride compound is prepared by treatment of the corresponding 1,2,3,4-tetrahydro-2,3-dioxoquinoxaline with chlorosulfonic acid pursuant to the method taught by Japanese Patent Application Publication Number 40-26,975 (see Chem. Abstr., 62, 11833d(1965)).

Starting material of formula IV wherein X is bromine can be prepared by reaction of the corresponding 1,2,3,4-tetrahydro-2,3-dioxoquinoxalinesulfonyl chloride with phosphorus oxybromide or phosphorus pentabromide at a temperature of from about 100°–150° C. according to the method disclosed by H. Dorn in "Preparative Organic Chemistry," ed. by G. Hilgetag and A. Martini, John Wiley and Sons, N.Y., 1972, p. 241–242.

Compounds of formula I wherein X is fluorine can be prepared by contacting a corresponding compound of formula I wherein X is chlorine or bromine with anhydrous potassium fluoride at a temperature of from about 150°–250° C. in a high-boiling, aprotic polar solvent, such as dimethyl sulfoxide or dimethyl sulfone. This method of preparation is a modification of the process for preparing fluoropyridines from other halopyridines described by G. C. Finger et al., J. Org. Chem., 28, 1666(1963)).

The invention is further illustrated by the following examples in which all temperatures are degrees C and all percentages are by weight unless otherwise stated.

EXAMPLE 1

2,3,7-Trichloro-6-quinoxalinesulfonic Acid, 2,2,2-Trifluoroethyl Ester

To a stirred mixture of 470 g (1.42 mole) of 2,3,7-trichloro-6-quinoxalinesulfonyl chloride and 153 g (1.53 mole) of 2,2,2-trifluoroethanol in 3 liters of anhydrous tetrahydrofuran are added 183 g (1.42 mole) of N,N-diisopropylethylamine. The resulting mixture is heated under reflux with exclusion of moisture for 24 hours. The solvent is removed under reduced pressure to obtain a residue which is dispersed in one liter of diethyl ether. The resulting mixture is washed twice with 500 ml of water then dried over magnesium sulfate, and filtered. The filtrate obtained therefrom is evaporated to give crude product which is recrystallized first from cyclohexane and then from 2-propanol to give 112 g (20%) of nearly colorless crystals having a melting point of 142°–144°.

Elemental Analysis (%): Calculated for $C_{10}H_4Cl_3F_3N_2O_3S$: C, 30.36; H, 1.02; N, 7.08; Cl, 26.89. Found: C, 30.5; H, 1.35; N, 6.85; Cl, 27.1.

Using a procedure similar to Example 1 with the appropriate compound of Formula IV and a suitable haloalcohol the compounds listed in Tables I and II can be prepared.

TABLE I 2,3-Dihalo-6-quinoxalinesulfonic Acids, Haloalkyl Esters

| X | Y | Z | R | mp (°C.) |
|---|---|---|---|---|
| Cl | H | H | $CF_3$ | 98–100 |
| Cl | 5-F | H | $CF_3$ | |
| Cl | 7-F | H | $CF_3$ | 106–108 |
| Cl | 8-F | H | $CF_3$ | |
| Cl | 5-Cl | H | $CF_3$ | |
| Cl | 7-Cl | H | $CF_3$ | 142–144 |
| Cl | 8-Cl | H | $CF_3$ | |
| Cl | 5-Br | H | $CF_3$ | |
| Cl | 7-Br | H | $CF_3$ | |
| Cl | 8-Br | H | $CF_3$ | |
| Cl | 5-$CH_3$ | H | $CF_3$ | |
| Cl | 7-$CH_3$ | H | $CF_3$ | 114–117 |
| Cl | 8-$CH_3$ | H | $CF_3$ | |
| Cl | 5-$CF_3$ | H | $CF_3$ | |
| Cl | 7-$CF_3$ | H | $CF_3$ | |
| Cl | 8-$CF_3$ | H | $CF_3$ | |
| Cl | 5-$CCl_3$ | H | $CF_3$ | |
| Cl | 7-$CCl_3$ | H | $CF_3$ | |
| Cl | 8-$CCl_3$ | H | $CF_3$ | |
| Cl | 5-$NO_2$ | H | $CF_3$ | |
| Cl | 7-$NO_2$ | H | $CF_3$ | |
| Cl | 8-$NO_2$ | H | $CF_3$ | |
| Cl | H | H | $CF_2CF_3$ | 105–107 |
| Cl | H | H | $(CF_2)_2CF_3$ | 116–120 |
| Cl | H | H | $(CF_2)_3CF_2H$ | 91–92 |
| Cl | 7-Cl | H | $CF_2CF_3$ | 144–145 |

TABLE I-continued 2,3-Dihalo-6-quinoxalinesulfonic Acids, Haloalkyl Esters

| X | Y | Z | R | mp (°C.) |
|---|---|---|---|---|
| Cl | 7-Cl | H | $(CF_2)_2CF_3$ | 144–147 |
| Cl | 7-F | H | $CF_2CF_3$ | 113–115 |
| Cl | 7-F | H | $(CF_2)_2CF_3$ | 119–120 |
| Cl | 7-CH$_3$ | H | $CF_2CF_3$ | 119–121 |
| Cl | 7-CH$_3$ | H | $(CF_2)_2CF_3$ | 116–117 |
| Cl | 7-Cl | 5-F | $CF_3$ | |
| Cl | 7-Cl | 8-F | $CF_3$ | |
| Cl | 7-Cl | 5-Cl | $CF_3$ | |
| Cl | 7-Cl | 8-Cl | $CF_3$ | |
| Cl | 7-Cl | 5-Br | $CF_3$ | |
| Cl | 7-Cl | 8-Br | $CF_3$ | |
| Cl | 7-Cl | 5-CH$_3$ | $CF_3$ | |
| Cl | 7-Cl | 8-CH$_3$ | $CF_3$ | |
| Cl | 7-Cl | 5-CF$_3$ | $CF_3$ | |
| Cl | 7-Cl | 8-CF$_3$ | $CF_3$ | |
| Cl | 7-Cl | 5-CCl$_3$ | $CF_3$ | |
| Cl | 7-Cl | 8-CCl$_3$ | $CF_3$ | |
| Cl | H | H | $CCl_3$ | 102–103 |
| Cl | 7-F | H | $CCl_3$ | 133–134 |
| Cl | 7-Cl | H | $CCl_3$ | 57–60 |
| Br | H | H | $CF_3$ | |
| Br | H | H | $CF_2CF_3$ | |
| Br | H | H | $(CF_2)_3CF_2H$ | |
| Br | 7-Cl | H | $CF_3$ | |
| Br | 7-F | H | $CF_3$ | |
| Br | 7-CH$_3$ | H | $CF_3$ | |

TABLE II 2,3-Dihalo-5-quinoxalinesulfonic Acids, Haloalkyl Esters

| X | Y | Z | R | m.p. (°C.) |
|---|---|---|---|---|
| Cl | H | H | $CF_3$ | |
| Cl | 6-F | H | $CF_3$ | |
| Cl | 7-F | H | $CF_3$ | |
| Cl | 8-F | H | $CF_3$ | |
| Cl | 6-Cl | H | $CF_3$ | |
| Cl | 7-Cl | H | $CF_3$ | |
| Cl | 8-Cl | H | $CF_3$ | |
| Cl | 6-Br | H | $CF_3$ | |
| Cl | 7-Br | H | $CF_3$ | |
| Cl | 8-Br | H | $CF_3$ | |
| Cl | 6-CH$_3$ | H | $CF_3$ | |
| Cl | 7-CH$_3$ | H | $CF_3$ | |
| Cl | 8-CH$_3$ | H | $CF_3$ | |
| Cl | 6-CF$_3$ | H | $CF_3$ | |
| Cl | 7-CF$_3$ | H | $CF_3$ | |
| Cl | 8-CF$_3$ | H | $CF_3$ | |
| Cl | 6-CCl$_3$ | H | $CF_3$ | |
| Cl | 7-CCl$_3$ | H | $CF_3$ | |
| Cl | 8-CCl$_3$ | H | $CF_3$ | |
| Cl | 6-NO$_2$ | H | $CF_3$ | |
| Cl | 7-NO$_2$ | H | $CF_3$ | |
| Cl | 8-NO$_2$ | H | $CF_3$ | |
| Cl | H | H | $CF_2CF_3$ | |
| Cl | H | H | $(CF_2)_2CF_3$ | |
| Cl | H | H | $(CF_2)_3CF_2H$ | |
| Cl | 7-Cl | 6-F | $CF_3$ | |
| Cl | 7-Cl | 8-F | $CF_3$ | |
| Cl | 7-Cl | 6-Cl | $CF_3$ | |
| Cl | 7-Cl | 8-Cl | $CF_3$ | |
| Cl | 7-Cl | 6-Br | $CF_3$ | |
| Cl | 7-Cl | 8-Br | $CF_3$ | |
| Cl | 7-Cl | 6-CH$_3$ | $CF_3$ | |
| Cl | 7-Cl | 8-CH$_3$ | $CF_3$ | |
| Cl | 7-Cl | 6-CF$_3$ | $CF_3$ | |
| Cl | 7-Cl | 8-CF$_3$ | $CF_3$ | |
| Cl | 7-Cl | 6-CCl$_3$ | $CF_3$ | |
| Cl | 7-Cl | 8-CCl$_3$ | $CF_3$ | |
| Cl | 6-CH$_3$ | 7-CH$_3$ | $CF_3$ | 82°–92° |
| Cl | 6-CH$_3$ | 7-CH$_3$ | $CCl_3$ | |
| Br | H | H | $CF_3$ | |
| Br | 6-Cl | 7-Cl | $CF_3$ | |
| Br | 6-CH$_3$ | 7-CH$_3$ | $CF_3$ | |

EXAMPLE 2

2,3-Difluoro-6-quinoxalinesulfonic Acid, 2,2,2-Trifluoroethyl Ester

A mixture of 36 g (0.10 mole) of 2,3-dichloro-6-quinoxalinesulfonic acid, 2,2,2-trifluoroethyl ester, and 100 g of dimethyl sulfone is heated to 110° and 23 g (0.40 mole) of anhydrous potassium fluoride are added thereto. The temperature of the resulting reaction mixture is raised to 200° and held there until the reaction is complete as determined by thin layer chromatography. The reaction mixture is cooled and then added to 500 ml of warm water to obtain a resulting mixture which is extracted with diethyl ether to give 2,3-difluoro-6-quinoxalinesulfonic acid, 2,2,2-trifluoroethyl ester.

Using a procedure similar to Example 2 with the appropriate compound of formula I compounds listed in Tables III and IV can be prepared.

TABLE III 2,3-Difluoro-6-quinoxalinesulfonic Acids, Haloalkyl Esters

| Y | Z | R |
|---|---|---|
| H | H | $CF_3$ |
| 7-Cl | H | $CF_3$ |
| 7-Cl | H | $CF_2CF_3$ |
| H | H | $CF_3$ |
| H | H | $CCl_3$ |

TABLE IV 2,3-Difluoro-5-quinoxalinesulfonic Acids, Haloalkyl Esters

| Y | Z | R |
|---|---|---|
| H | H | $CF_3$ |

TABLE IV-continued 2,3-Difluoro-5-quinoxalinesulfonic Acids, Haloalkyl Esters

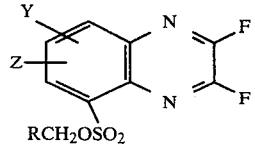

| Y | Z | R |
|---|---|---|
| 6-Cl | 7-Cl | CF₃CF₃ |
| 6-Cl | 7-Cl | CF₃ |
| 6-CH₃ | 7-CH₃ | CF₃ |
| 6-CH₃ | 7-CH₃ | CCl₃ |

Formulations

Useful formulations of the compounds of Formula I can be prepared in conventional ways. They include dusts, suspensions, wettable powders, and the like. Many of them can be applied directly. Sprayable formulations can be extended in suitable media and used at spray volumes of from a few liters to several hundred liters per hectare. High strength compositions are used primarily as concentrates which are to be diluted prior to ultimate use. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the approximate proportions set forth in Table 8.

TABLE 8

| | Weight Percent* | | |
|---|---|---|---|
| | Active Ingredients | Diluent(s) | Surfactant(s) |
| Wettable Powders | 20–90 | 0–74 | 1–10 |
| Oil Suspensions, Emulsions | 5–50 | 40–95 | 0–15 |
| Aqueous Suspensions | 10–50 | 40–84 | 1–20 |
| Dusts | 1–25 | 70–99 | 0–5 |
| High Strength Compositions | 90–99 | 0–10 | 0–2 |

Lower or high levels of active ingredient can be present, depending on the intended use and the physical properties of the compound. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, New Jersey, but other solids, either mined or manufactured, can be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually grinding, as in a hammer or fluid energy mill. Suspensions are prepared by wet milling (see, for example, Littler, U.S. Pat. No. 3,060,084).

For further information regarding the art of formulation, see for example:
R. R. Shaffer, U.S. Pat. No. 3,560,616 Feb. 2, 1971, Col. 3 Line 48 through Col. 7 Line 26 and Examples 3–9, 11–18.
E. Somers, "Formulation", Chapter 6 in Torgeson, "Fungicides", Vol. I, Academic Press, New York, 1967.

EXAMPLE 3

Wettable Powder 2,3,7-trichloro-6-quinoxalinesulfonic acid 2,2,2-trifluoroethyl ester:50%
sodium alkylnaphthalenesulfonate:3%
sodium N-methyl-N-oleoyltaurate:2%
diatomaceous earth:45%

The ingredients can be blended, coarsely hammer-milled and then air milled to produce particles of active essentially all below 10 microns in diameter. The product can be reblended before packaging.

EXAMPLE 4

Oil Dispersible Powder 2,3-dichloro-7-fluoro-6-quinoxaline sulfonic acid 2,2,3,3,4,4,4-heptafluorobutyl ester:40%
sodium dodecyl benzene sulfonate:3%
polyvinyl pyrrolidone:1%
amorphous silica:1%
starch:55%

The ingredients can be thoroughly blended, passed through an air mill to produce an average particle size under 15 microns, reblended, and sifted through a U.S.S. No. 50 sieve (0.3 mm opening) before packaging. This formulation can be dispersed into an aliphatic oil prior to spraying on crops.

EXAMPLE 5

Dust 2,3-dichloro-7-fluoro-6-quinoxalinesulfonic acid, 2,2,3,3,3 pentafluoropropyl ester:10%
attapulgite:10%
talc:80%

The active ingredient can be blended with attapulgite and then passed through a hammer mill to produce particles substantially all below 200 microns in diameter. This ground concentrate can be then blended with powdered talc until homogeneous.

EXAMPLE 6

High Strength Concentrate 2,3-dichloro-6-quinoxalinesulfonic acid, 2,2,2-trifluoroethyl ester:98.5%
silica aerogel:0.5%
synthetic amorphous fine silica:1.0%

The ingredients can be blended and ground in a hammer mill to produce a high strength concentrate practically all passing a U.S.S. No. 50 sieve (0.3 mm openings). This material may then be formulated in a variety of ways.

Utility

The compounds of this invention are effective for the control of a broad spectrum of plant diseases on a variety of host plants with a margin of plant safety. The diseases are incited by fungal pathogens represented by, but not limited to, *Venturia inaequalis, Cercospora beticola, Plasmorpara viticola, Piricularia oryzae, Phytophthora infestans, Uromyces phaseoli, Gymnosproangium juniperi-virginianae, Puccinia graminis,* and *Erisyphe chicoracearum.*

Disease control is accomplished by applying the compounds of this invention to the portion of the plant to be protected. The compounds are applied as a preventive treatment prior to inoculation with the pathogen.

Rates of application for compounds of this invention will be influenced by specific host plants, fungal pathogens, and many factors of the environment and must be determined under use conditions. Foliage sprayed with concentrations ranging from 1 to 500 ppm active ingredient can be protected from disease under suitable conditions. Compositions of this invention may contain, in addition to compounds of this invention, conventional pesticides, such as insecticides, miticides, bactericides, nematicides, fungicides, or other agricultural chemicals such as growth modifying agents and fertilizer ingredients, and the like. The proper choice of conventional pesticide and their amounts can be made by one skilled in the art of protecting plants from pest degradation.

The following are illustrative of other fungicides that may be included in compositions or added to sprays containing one or more of the active compound of this invention:

bis(dimethylthiocarbamoyl)disulfide; or tetramethylthiuram disulfide (thiram);
metal salts of ethylenebisdithiocarbamic acid or propylenebisdithiocarbamic acids, e.g. manganese, zinc, iron and sodium salts (maneb or zineb);
n-dodecylguanidine acetate (dodine);
N-(trichloromethylthio)phthalimide (folpet);
N-[(trichloromethyl)thio]-4-cyclohexene-1,2-dicarboximide (captan);
cis-N-[(1,1,2,2-tetrachloroethyl)thio]-4-cyclohexene-1,2-dicarboximide (captafol);
2,4-dichloro-6-(o-chloroanilino)-α-triazine ("Dyrene");
3,3'-ethylenebis(tetrahydro-4,6-dimethyl-2H-1,3,5-thiadiazine-2-thione) (milneb);
triphenyltin hydroxide (fentin hydroxide);
triphenyltin acetate (fentin acetate);
N'-dichlorofluoromethylthio-N,N-dimethyl-N'-phenylsulfamide (dichlorfluanid);
tetrachloroisophthalonitrile (chlorothalonil);
tribasic copper sulfate;
fixed copper;
sulfur;
methyl 1-(butylcarbamoyl)-2-benzimidazolecarbamate (benomyl);
methyl 2-benzimidazolecarbamate (carbendazim);
1,2-bis(3-methoxycarbonyl-2-thiouredio)benzene (methyl thiophanate);
2-cyano-N-(ethylcarbamoyl)-2-methoxyiminoacetamide;
methyl d,l-N-(2,6-dimethylphenyl)-N-(2'-methoxyacetyl)alaninate;
1-(4-chlorophenoxy)-3,3-dimethyl-1-(1,2,4-triazol-1-yl)butane-2-one (triadimefon);
α-butyl-α-phenyl-1H-imidazole-1-propanenitrile;
N-(3',5'-dichlorophenyl)-1,2-dimethylcyclopropane-1,2-dicarboximide (procymidone).

The agricultural chemicals listed above are merely exemplary of compounds that may be mixed with the active compounds of the invention to broaden the spectrum of disease control.

In the following examples, which more clearly illustrate the biological activity of the compounds of this invention, percent disease control was calcuated by the formula $$100 - [\frac{\text{disease rating on treated}}{\text{disease rating on untreated}} \times 100] = \text{percent control}$$

No plant injury was noted when host plants specified in the following examples were treated with compounds of this invention at the specified application rates.

EXAMPLE 7

Compounds of the invention are dissolved in acetone in an amount equal to 10% of the final volume and then suspended at a concentration of 16 ppm in purified water containing 250 ppm of Trem ® 014 surfactant which consists of nonionic polyhydric alcohol esters and is manufactured by Nopco Chemical Division of Diamond Shamrock. This suspension is sprayed to the point of runoff on seedling apple plants. The following day, the plants are inoculated with a spore suspension of the fungus *Venturia inaequalis* and incubated in a saturated humidity chamber at 20° C. for 24 hours, and then in a greenhouse for an additional 11 days before disease ratings are made. As shown in the following table, compounds of this invention provide excellent disease control, as treated plants have only a few foliar lesions in contrast to untreated plants which are covered with scab lesions.

| Compound | Percent Control apple scab |
| --- | --- |
| 2,3,7-trichloro-6-quinoxaline-sulfonic acid, 2.2.2-trifluoro-ethyl ester | 99 |
| 2,3-dichloro-7-fluoro-6-quinoxaline-sulfonic acid, 2,2,2-trifluoro-ethyl ester | 99 |
| 2,3-dichloro-7-fluoro-6-quinoxalinesulfonic acid, 2,2,3,3,3-pentafluoropropyl ester | 100 |
| 2,3,7-trichloro-6-quinoxaline-sulfonic acid, 2,2,3,3,3-pentafluoropropyl ester | 99 |
| 2,3-dichloro-6-quinoxalinesulfonic acid, 2,2,3,3,3-pentafluoropropyl ester | 92 |
| 2,3-dichloro-7-fluoro-6-quinoxaline-sulfonic acid, 2,2,3,3,4,4,4-heptafluorobutyl ester | 94 |
| 2,3-dichloro-7-fluoro-6-quinoxaline-sulfonic acid, 2,2,2-trichloro-ethyl ester | 84 |
| 2,3-dichloro-7-fluoro-6-quinoxaline-sulfonic acid, 2,2,3,3,4,4,5,5-octafluoropentyl ester | 77 |
| 2,3-dichloro-7-methyl-6-quinoxaline-sulfonic acid, 2,2,2-trifluoroethyl ester | 99 |
| 2,3-dichloro-7-methyl-6-quinoxaline-sulfonic acid, 2,2,3,3,3-pentafluoropropyl ester | 97 |
| 2,3-dichloro-6-quinoxaline-sulfonic acid, 2,2,2-trichloroethyl ester | 91 |
| 2,3-dichloro-6-quinoxalinesulfonic | |

| Compound | Percent Control apple scab |
|---|---|
| acid, 2,2,2-trifluoroethyl ester | 57 |

The compound 2,3,7-trichloro-6-quinoxalinesulfonic acid, 2,2,2-trichloroethyl ester is similarly tested except that it is suspended at a concentration of 100 ppm in purified water containing 250 ppm of Trem ® 014 surfactant and the plants, after incubation in the humidity chamber, are incubated in a greenhouse 8 days before disease ratings are made. This compound provides 100% disease control, as there are no lesions on the treated plants in contrast to untreated plants which are covered with scab lesions.

EXAMPLE 8

2,3,7-trichloro-6-quinoxalinesulfonic acid, 2,2,2-trifluoroethyl ether is dissolved in acetone in an amount equal to 10% of the final volume and then suspended at a concentration of 400 ppm in purified water containing 500 ppm of Trem ® 014 surfactant. This suspension is sprayed to the point of run-off on 6-8 week-old sugar beet seedlings. The following day, the seedlings are inoculated with a spore suspension of the fungus *Cercospora beticola* and incubated in a saturated humidity chamber at 22°-26° for 72 hours. After 21 days additional incubation in a greenhouse, disease ratings are made. The plants treated with 2,3,7-trichloro-6-quinoxalinesulfonic acid, 2,2,2-trifluoroethyl ester have only a few foliar lesions (92% control) in contrast to untreated plants which have numerous leafspot lesions on each leaf.

EXAMPLE 9

Compounds of the invention are dissolved in acetone in an amount equal to 10% of the final volume and then suspended at a concentration of 80 ppm in purified water containing 250 ppm of Trem ® 014 surfactant. This suspension is sprayed to the point of run-off on seedling grape plants. The following day, plants are inoculated with a spore suspension of the fungus *Plasmopara viticola* and incubated in a saturated humidity chamber of 20° for 48 hours, then in a greenhouse for an additional 5 days, and finally in a saturated humidity chamber at 20° for an additional 48 hours before disease ratings are made. As shown in the following table, compounds of this invention provide excellent disease control, as treated plants are either completely free of or have only a few foliar lesions in contrast to untreated plants which are covered with downy mildew.

| Compound | Percent Control Grape Downy Mildew |
|---|---|
| 2,3,7-trichloro-6-quinoxaline-sulfonic acid, 2,2,2-trifluoro-ethyl ester | 100 |
| 2,3-dichloro-7-fluoro-6-quinoxaline-sulfonic acid, 2,2,2-trifluoro-ethyl ester | 100 |
| 2,3-dichloro-7-fluoro-6-quinoxaline-sulfonic acid, 2,2,3,3,3-pentafluoropropyl ester | 93 |
| 2,3-dichloro-6-quinoxaline-sulfonic acid, 2,2,3,3,3-pentafluoropropyl ester | 47 |
| 2,3-dichloro-7-fluoro-6-quinoxaline-sulfonic acid, 2,2,3,3,4,4,4-heptafluorobutyl ester | 100 |
| 2,3-dichloro-7-fluoro-6-quinoxaline-sulfonic acid, 2,2,3,3,4,4,5,5,-octafluoropentyl ester | 63 |

EXAMPLE 10

Compounds of the invention are dissolved in acetone in an amount equal to 10% of the final volume and then suspended at a concentration of 80 ppm in purifier water containing 250 ppm of Trem ® 014 surfactant. This suspension is sprayed to the point of run-off on rice seedlings. The following day, the rice seedlings are inoculated with a spore suspension of the fungus *Piricularia oryzae* and incubated in a saturated humidity chamber at 23° C. for 24 hours, and then in a greenhouse for an additional 7 days before disease ratings are made. As shown in the following table, compounds of this invention provide excellent disease control, as treated plants are either completely free of or have only a few foliar lesions in contrast to untreated plants which have numerous blast lesions on each leaf.

| Compound | Percent Control Rice Blast |
|---|---|
| 2,3,7-trichloro-6-quinoxaline-sulfonic acid, 2,2,2-trifluoro-ethyl ester | 98 |
| 2,3-dichloro-7-fluoro-6-quinoxaline-sulfonic acid, 2,2,2-trifluoroethyl ester | 100 |
| 2,3-dichloro-6-quinoxalinesulfonic acid, 2,2,2-trichloroethyl ester | 96 |
| 2,3-dichloro-7-fluoro-6-quinoxaline-sulfonic acid, 2,2,3,3,3-pentafluoropropyl ester | 92 |
| 2,3,7-trichloro-6-quinoxaline-sulfonic acid, 2,2,3,3,3-pentafluoropropyl ester | 96 |
| 2,3-dichloro-6-quinoxalinesulfonic acid, 2,2,3,3,3-pentafluoropropyl ester | 97 |
| 2,3-dichloro-7-fluoro-6-quinoxaline-sulfonic acid, 2,2,3,3,4,4,4-heptafluorobutyl ester | 87 |
| 2,3-dichloro-7-fluoro-6-quinoxaline-sulfonic acid, 2,2,3,3,4,4,5,5-octafluoropentyl ester | 97 |

EXAMPLE 11

Compounds of the invention are dissolved in acetone in an amount equal to 10% of the final volume and then suspended at a concentration of 80 ppm in purified water containing 250 ppm of Trem ® 014 surfactant. This suspension is sprayed to the point of run-off on 6-week-old tomato plants. The following day the plants are inoculated with a spore suspension of *Phytophthora infestans* and incubated in a saturated humidity chamber at 20° for 24 hours and then in a greenhouse for an additional 4 days before disease ratings are made. As shown in the following table most compounds of this invention provide excellent disease control as treated plants have only a few foliar lesions in contrast to untreated plants which are covered with late blight lesions.

| Compound | Percent Control Tomato Late Blight |
|---|---|
| 2,3-dichloro-6-quinoxalinesulfonic acid, 2,2,2-trichloroethyl ester | 99 |
| 2,3,7-trichloro-6-quinoxalinesulfonic acid, 2,2,2-trifluoroethyl ester | 68 |
| 2,3-dichloro-7-fluoro-6-quinoxalinesulfonic acid, 2,2,2-trifluoroethyl ester | 94 |
| 2,3-dichloro-7-fluoro-6-quinoxalinesulfonic acid, 2,2,3,3,3-pentafluoropropyl ester | 91 |
| 2,3,7-trichloro-6-quinoxalinesulfonic acid, 2,2,3,3,3-pentafluoropropyl ester | 18 |
| 2,3-dichloro-6-quinoxalinesulfonic acid, 2,2,3,3,3-pentafluoropropyl ester | 86 |

EXAMPLE 12

Compounds of the invention are dissolved in acetone in an amount equal to 10% of the final volume and then suspended at a concentration of 16 ppm in purified water containing Trem ® 014 surfactant. This suspension is sprayed to the point of run-off on Pinto bean seedlings. The following day, the plants are inoculated with a spore suspension of the fungus *Uromyces phaseoli* var. *typica* and incubated in a saturated humidity chamber at 20° for 24 hours, and then in a greenhouse for an additional 7 days before disease ratings are made. As shown in the following table, the compounds of this invention provide excellent disease control, as treated plants have only a few rust pustules in contrast to untreated plants which had numerous rust pustules on each leaf.

| Compound | Percent Control Bean Rust |
|---|---|
| 2,3,7-trichloro-6-quinoxalinesulfonic acid, 2,2,2-trifluoroethyl ester | 98 |
| 2,3-dichloro-7-fluoro-6-quinoxalinesulfonic acid, 2,2,2-trifluoroethyl ester | 97 |
| 2,3-dichloro-7-fluoro-6-quinoxalinesulfonic acid, 2,2,3,3,3-pentafluoropropyl ester | 99 |
| 2,3,7-trichloro-6-quinoxalinesulfonic acid, 2,2,3,3,3-pentafluoropropyl ester | 89 |
| 2,3-dichloro-6-quinoxalinesulfonic acid, 2,2,3,3,3-pentafluoropropyl ester | 44 |
| 2,3-dichloro-7-fluoro-6-quinoxalinesulfonic acid, 2,2,3,3,4,4,4-heptafluorobutyl ester | 94 |
| 2,3-dichloro-7-fluoro-6-quinoxalinesulfonic acid, 2,2,3,3,4,4,5,5,-octafluoropentyl ester | 90 |

EXAMPLE 13

Compounds of the invention are dissolved in acetone in an amount equal to 10% of the final volume and then suspended at a concentration of 16 ppm in purified water containing 250 ppm of Trem ® 014 surfactant. This suspension is sprayed to the point of run-off on seedling apple plants. The following day, the plants are inoculated with a spore suspension of the fungus *Gymnosporangium juniperi-virginianae* and incubated in a saturated humidity chamber at 20° for 24 hours and then in a greenhouse for an additional 10 days before disease ratings are made. As shown in the following table, the compounds of this invention provide excellent disease control, as treated plants have a few rust pustules in contrast to untreated plants which had numerous rust pustules on each leaf.

| Compound | Percent Control Cedar-Apple Rust |
|---|---|
| 2,3,7-trichloro-6-quinoxalinesulfonic acid, 2,2,2-trifluoroethyl ester | 91 |
| 2,3-dichloro-7-fluoro-6-quinoxalinesulfonic acid, 2,2,2-trifluoroethyl ester | 90 |
| 2,3-dichloro-7-fluoro-6-quinoxalinesulfonic acid, 2,2,3,3,3-pentafluoropropyl ester | 87 |
| 2,3,7-trichloro-6-quinoxalinesulfonic acid, 2,2,3,3,3-pentafluoropropyl ester | 98 |
| 2,3-dichloro-6-quinoxalinesulfonic acid, 2,2,3,3,3-pentafluoropropyl ester | 100 |

EXAMPLE 14

Compounds of the invention are dissolved in acetone in an amount equal to 10% of the final volume and then suspended at a concentration of 80 ppm in purified water containing 250 ppm of Trem ® 014 surfactant. This suspension is sprayed to the point of run-off on wheat seedlings. The following day, the plants are inoculated with a spore suspension of *Puccinia graminis* var. *tritici* and incubated in a saturated humidity chamber at 20° for 24 hours and then in a greenhouse for an additional 7 days before disease ratings are made. As shown in the following table, most of the compounds of this invention provide excellent disease control, as treated plants have only a few rust pustules in contrast to untreated plants which have numerous rust pustules on each leaf.

| Compound | Percent Control Wheat Rust |
|---|---|
| 2,3,7-trichloro-6-quinoxalinesulfonic acid, 2,2,2-trifluoroethyl ester | 93 |
| 2,3-dichloro-7-fluoro-6-quinoxalinesulfonic acid, 2,2,2-trifluoroethyl ester | 98 |
| 2,3-dichloro-7-fluoro-6-quinoxalinesulfonic acid, 2,2,3,3,3-pentafluoropropyl ester | 99 |
| 2,3,7-trichloro-6-quinoxalinesulfonic acid, 2,2,3,3,3-pentafluoropropyl ester | 58 |
| 2,3-dichloro-6-quinoxalinesulfonic acid, 2,2,3,3,3-pentafluoropropyl ester | 77 |
| 2,3-dichloro-7-fluoro-6-quinoxalinesulfonic acid, 2,2,3,3,4,4,4-heptafluorobutyl ester | 18 |
| 2,3-dichloro-7-fluoro-6-quinoxalinesulfonic acid, 2,2,3,3,4,4,5,5-octafluoropentyl ester | 50 |
| 2,3-dichloro-7-methyl-6-quinoxalinesulfonic acid, 2,2,2-trifluoroethyl ester | 67 |
| 2,3-dichloro-7-methyl-6-quinoxalinesulfonic acid, 2,2,3,3,3-pentafluoropropyl ester | 94 |
| 2,3-dichloro-6-quinoxalinesulfonic acid, 2,2,2-trifluoroethyl ester | 98 |

| Compound | Percent Control Wheat Rust |
| --- | --- |
| 2,3-dichloro-6-quinoxalinesulfonic acid, 2,2,2-trichloroethyl ester | 50–70 |
| 2,3-dichloro-7-fluoro-6-quinoxalinesulfonic acid, 2,2,2-trichloroethyl ester | 90 |

EXAMPLE 15

Compounds of the invention are dissolved in acetone in an amount equal to 6% of the final volume and then suspended at a concentration of 100 ppm in purified water containing 250 ppm of Trem ® 014 surfactant. This suspension is sprayed to the point of run-off on one-week old Straight-Eight variety cucumber plants. The following day, the plants are inoculated with a spore suspension of the fungus *Erisyphe chicoracearum* (Cucumber Powdery Mildew) and incubated in a greenhouse for 7 days before disease ratings are made.

As shown in the following table, the compounds tested provide disease control with little or no phytotoxicity, as treated plants have only a few foliar lesions in contrast to untreated plants which are covered with powdery mildew.

| Compound | Percent Control Cucumber Powdery Mildew |
| --- | --- |
| 2,3-dichloro-6,7-dimethyl-5-quinoxalinesulfonic acid, 2,2,3,3,4,4,4-heptafluoro-butyl ester | 100 |
| 2,3-dichloro-7-nitro-5-quinoxalinesulfonic acid, 2,2,2-trifluoroethyl ester mixed with the 6-quinoxalinesulfonic acid isomer | 100 |
| 2,3-dichloro-7-nitro-5-quinoxalinesulfonic acid, 2,2,3,3,4,4,5,5-octafluoropentyl ester mixed with the 6-quinoxalinesulfonic acid isomer | 100 |
| 2,3-dichloro-7-nitro-5-quinoxalinesulfonic acid, 2,2,3,3,4,4,4-heptafluorobutyl ester mixed with the 6-quinoxalinesulfonic acid isomer | 100 |

What is claimed is:

1. A compound having the formula

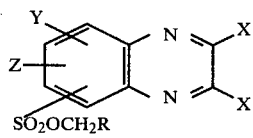

wherein
X is F, Cl, or Br;
R is fluoroalkyl of 1–4 carbon atoms and 1–9 fluorine atoms;
Y is H, F, Cl, Br, $CH_3$, $CF_3$, $CCl_3$, or $NO_2$; and
Z is H, F, Cl, Br, $CH_3$, $CF_3$, or $CCl_3$.

2. A compound of claim 1 wherein X is Cl.
3. A compound of claim 1 wherein $RCH_2OSO_2$ is a 6-substituent.
4. A compound of claim 1 wherein Z is H.
5. A compound of claim 2 wherein $RCH_2OSO_2$ is a 6-substituent.
6. A compound of claim 5 wherein Z is H.
7. A compound of claim 5 wherein R is perfluoroalkyl of 1–4 carbon atoms or —$(CF_2)_3CHF_2$.
8. A compound of claim 6 wherein R is perfluoroalkyl of 1–4 carbon atoms or —$(CF_2)_3CHF_2$.
9. A compound of claim 7 wherein Y is H, F, Cl or $CH_3$.
10. A compound of claim 8 wherein Y is H, F, Cl or $CH_3$.
11. A compound of claim 10 wherein Y is a 7-substituent and R if $CF_3$.
12. A compound of claim 1 which is 2,3,7-trichloro-6-quinoxalinesulfonic acid, 2,2,2-trifluoroethyl ester.
13. A compound of claim 1 which is 2,3-dichloro-7-fluoro-6-quinoxalinesulfonic acid, 2,2,2-trifluoroethyl ester.
14. A compound of claim 1 which is 2,3-dichloro-7-fluoro-6-quinoxalinesulfonic acid, 2,2,3,3,3-pentafluoropropyl ester.
15. A compound of claim 1 which is 2,3,7-trichloro-6-quinoxalinesulfonic acid, 2,2,3,3,3-pentafluoropropyl ester.
16. A compound of claim 1 which is 2,3-dichloro-6-quinoxalinesulfonic acid, 2,2,3,3,3,-pentafluoropropyl ester.
17. A compound of claim 1 which is 2,3-dichloro-7-fluoro-6-quinoxalinesulfonic acid, 2,2,3,3,4,4,4-heptafluorobutyl ester.
18. A compound of claim 1 which is 2,3-dichloro-7-fluoro-6-quinoxalinesulfonic acid, 2,2,3,3,4,4,5,5-octafluoropentyl ester.
19. A compound of claim 1 which is 2,3-dichloro-7-methyl-6-quinoxalinesulfonic acid, 2,2,2-trifluoroethyl ester.
20. A compound of claim 1 which is 2,3-dichloro-7-methyl-6-quinoxalinesulfonic acid, 2,2,3,3,3-pentafluoropropyl ester.
21. A compound of claim 1 which is 2,3-dichloro-6-quinoxalinesulfonic acid, 2,2,2-trifluoroethyl ester.
22. A fungicidal composition consisting essentially of a fungicidally effective amount of a compound of claim 1 and at least one of (a) a surfactant and (b) a suitable diluent.
23. A fungicidal composition consisting essentially of a fungicidally effective amount of a compound of claim 2 and at least one of (a) a surfactant and (b) a suitable diluent.
24. A fungicidal composition consisting essentially of a fungicidally effective amount of a compound of claim 3 and at least one of (a) a surfactant and (b) a suitable diluent.
25. A fungicidal composition consisting essentially of a fungicidally effective amount of a compound of claim 4 and at least one of (a) a surfactant and (b) a suitable diluent.
26. A fungicidal composition consisting essentially of a fungicidally effective amount of a compound of claim 5 and at least one of (a) a surfactant and (b) a suitable diluent.
27. A fungicidal composition consisting essentially of a fungicidally effective amount of a compound of claim 6 and at least one of (a) a surfactant and (b) a suitable diluent.
28. A fungicidal composition consisting essentially of a fungicidally effective amount of a compound of claim 7 and at least one of (a) a surfactant and (b) a suitable diluent.

29. A fungicidal composition consisting essentially of a fungicidally effective amount of a compound of claim 8 and at least one of (a) a surfactant and (b) a suitable diluent.

30. A fungicidal composition consisting essentially of a fungicidally effective amount of a compound of claim 9 and at least one of (a) a surfactant and (b) a suitable diluent.

31. A fungicidal composition consisting essentially of a fungicidally effective amount of a compound of claim 10 and at least one of (a) a surfactant and (b) a suitable diluent.

32. A fungicidal composition consisting essentially of a fungicidally effective amount of a compound of claim 11 and at least one of (a) a surfactant and (b) a suitable diluent.

33. A method for control of fungal disease of plants comprising applying to the locus where control is desired a fungicidally effective amount of a compound of claim 1.

34. A method for control of fungal disease of plants comprising applying to the locus where control is desired a fungicidally effective amount of a compound of claim 2.

35. A method for control of fungal disease of plants comprising applying to the locus where control is desired a fungicidally effective amount of a compound of claim 3.

36. A method for control of fungal disease of plants comprising applying to the locus where control is desired a fungicidally effective amount of a compound of claim 4.

37. A method for control of fungal disease of plants comprising applying to the locus where control is desired a fungicidally effective amount of a compound of claim 5.

38. A method for control of fungal disease of plants comprising applying to the locus where control is desired a fungicidally effective amount of a compound of claim 6.

39. A method for control of fungal disease of plants comprising applying to the locus where control is desired a fungicidally effective amount of a compound of claim 7.

40. A method for control of fungal disease of plants comprising applying to the locus where control is desired a fungicidally effective amount of a compound of claim 8.

41. A method for control of fungal disease of plants comprising applying to the locus where control is desired a fungicidally effective amount of a compound of claim 9.

42. A method for control of fungal disease of plants comprising applying to the locus where control is desired a fungicidally effective amount of a compound of claim 10.

43. A method for control of fungal disease of plants comprising applying to the locus where control is desired a fungicidally effective amount of a compound of claim 11.

* * * * *